(12) United States Patent
Leach et al.

(10) Patent No.: US 9,855,382 B2
(45) Date of Patent: Jan. 2, 2018

(54) CELL WASHING DEVICE USING STANDING ACOUSTIC WAVES AND A PHANTOM MATERIAL

(71) Applicant: Biomet Biologics, LLC, Warsaw, IN (US)

(72) Inventors: Michael D. Leach, Warsaw, IN (US); Ned M. Hamman, Leesburg, IN (US); David Abeskaron, Warsaw, IN (US); Grant D. Cunningham, Warsaw, IN (US); Randel Dorian, San Diego, CA (US); Richard W. Storrs, Berkeley, CA (US); Scott R. King, New Orleans, LA (US)

(73) Assignee: Biomet Biologics, LLC, Warsaw, IN (US)

( * ) Notice: Subject to any disclaimer, the term of this patent is extended or adjusted under 35 U.S.C. 154(b) by 109 days.

(21) Appl. No.: 14/674,089

(22) Filed: Mar. 31, 2015

(65) Prior Publication Data
US 2016/0287778 A1 Oct. 6, 2016

(51) Int. Cl.
*A61M 1/36* (2006.01)
*A61K 35/18* (2015.01)
(Continued)

(52) U.S. Cl.
CPC ........... *A61M 1/3692* (2014.02); *A61K 35/18* (2013.01); *A61M 1/0281* (2013.01);
(Continued)

(58) Field of Classification Search
CPC ... A61K 35/18; A61M 1/0281; A61M 1/3678; A61M 1/3692; A61M 2202/0429;
(Continued)

(56) References Cited

U.S. PATENT DOCUMENTS 4,710,162 A 12/1987 Johnson
4,759,775 A * 7/1988 Peterson ................ A61M 1/36
210/188
(Continued)

FOREIGN PATENT DOCUMENTS

WO WO-2012125470 A1 9/2012
WO WO-2012135663 A2 10/2012
(Continued)

OTHER PUBLICATIONS

International Search Report and Written Opinion dated Feb. 25, 2015 for PCT/US2014/061523 claiming benefit of U.S. Appl. No. 14/519,302, filed Oct. 21, 2014, U.S. Appl. No. 14/519,284, filed Oct. 21, 2014, U.S. Appl. No. 14/519,317, filed Oct. 21, 2014, claiming benefit of U.S. Appl. No. 62/011,992, filed Jun. 13, 2014, claiming priority of U.S. Appl. No. 61/979,695, filed Apr. 15, 2014, claiming priority of U.S. Appl. No. 61/893,555, filed Oct. 21, 2013.
(Continued)

*Primary Examiner* — Adam Marcetich
(74) *Attorney, Agent, or Firm* — Schwegman Lundberg & Woessner, P.A.

(57) ABSTRACT

Devices for washing a composition including cells are provided. The devices include a separation channel, a first wave component and a second wave component. The separation channel is positioned between the first and second wave components. Collectively, the wave components generate a standing bulk acoustic wave that isolates cells from the composition.

22 Claims, 13 Drawing Sheets

(51) Int. Cl.
| | |
|---|---|
| *C12N 5/078* | (2010.01) |
| *C12N 13/00* | (2006.01) |
| *A61M 1/02* | (2006.01) |
| *B01D 43/00* | (2006.01) |
| *B01D 21/28* | (2006.01) |
| *B01L 3/00* | (2006.01) |
| *B01L 9/00* | (2006.01) |

(52) U.S. Cl.
CPC ......... *A61M 1/3678* (2014.02); *B01D 21/283* (2013.01); *B01D 43/00* (2013.01); *B01L 3/502761* (2013.01); *C12N 5/0641* (2013.01); *C12N 13/00* (2013.01); *A61M 2202/0429* (2013.01); *A61M 2205/3375* (2013.01); *B01L 9/527* (2013.01); *B01L 2200/025* (2013.01); *B01L 2300/089* (2013.01); *B01L 2300/0874* (2013.01); *B01L 2300/0877* (2013.01); *B01L 2300/0887* (2013.01); *B01L 2400/0436* (2013.01)

(58) Field of Classification Search
CPC ........ A61M 2205/3375; A61M 1/3693; A61M 1/3695; A61M 1/3698; B01D 21/283; B01D 43/00; B01D 49/006; B01L 3/502761; B01L 2400/0433; B01L 2400/0436; B01L 2400/0439; C12N 13/00; C12N 5/0641; G01N 2015/142; G01N 2001/4094
See application file for complete search history.

(56) References Cited

U.S. PATENT DOCUMENTS

| | | | | |
|---|---|---|---|---|
| 5,039,426 | A * | 8/1991 | Giddings | B01D 21/00 209/127.1 |
| 5,225,089 | A | 7/1993 | Benes et al. | |
| 5,613,456 | A * | 3/1997 | Kuklinski | B63B 1/38 114/330 |
| 5,688,405 | A * | 11/1997 | Dickinson | B01D 21/283 210/170.09 |
| 5,834,625 | A * | 11/1998 | Kraus, Jr. | B01D 19/0078 73/32 R |
| 7,674,100 | B2 | 3/2010 | Hayes-Pankhurst et al. | |
| 7,837,040 | B2 | 11/2010 | Ward et al. | |
| 7,846,382 | B2 | 12/2010 | Strand et al. | |
| 8,535,536 | B1 * | 9/2013 | Gale | B01D 57/00 210/198.1 |
| 2002/0154571 | A1 * | 10/2002 | Cefai | B01D 21/283 367/13 |
| 2005/0100481 | A1 * | 5/2005 | Mae | B01F 13/0059 422/527 |
| 2005/0229696 | A1 * | 10/2005 | Takayama | B01F 5/0646 73/204.26 |
| 2006/0124555 | A1 * | 6/2006 | Nakatani | B01D 21/283 210/748.01 |
| 2007/0000814 | A1 * | 1/2007 | Kennedy | B03C 1/02 209/210 |
| 2007/0029257 | A1 * | 2/2007 | Mueth | A61M 1/36 210/645 |
| 2007/0091442 | A1 * | 4/2007 | MacDonald | B01L 3/502753 359/614 |
| 2008/0085227 | A1 * | 4/2008 | Miyamoto | B01F 5/0646 422/224 |
| 2008/0181828 | A1 | 7/2008 | Kluck | |
| 2009/0042239 | A1 * | 2/2009 | Ward | G01N 15/1404 435/29 |
| 2009/0066936 | A1 | 3/2009 | Huang et al. | |
| 2009/0139931 | A1 * | 6/2009 | Leonard | A61M 1/14 210/645 |
| 2009/0158823 | A1 * | 6/2009 | Kaduchak | G01N 15/1404 73/61.75 |
| 2009/0178716 | A1 * | 7/2009 | Kaduchak | G01N 15/1404 137/13 |
| 2010/0139377 | A1 | 6/2010 | Huang et al. | |
| 2011/0105982 | A1 * | 5/2011 | Leonard | A61M 1/14 604/6.01 |
| 2011/0136645 | A1 | 6/2011 | Ellingboe et al. | |
| 2011/0207238 | A1 * | 8/2011 | Horii | B01L 3/50273 436/518 |
| 2012/0196314 | A1 | 8/2012 | Nawaz et al. | |
| 2013/0043170 | A1 * | 2/2013 | Rose | B01D 21/283 209/659 |
| 2013/0048565 | A1 | 2/2013 | Fiering et al. | |
| 2013/0175226 | A1 * | 7/2013 | Coussios | B01D 21/283 210/748.05 |
| 2014/0065117 | A1 | 3/2014 | Gray | |
| 2014/0147860 | A1 * | 5/2014 | Kaduchak | G01N 33/56966 435/7.21 |
| 2014/0193381 | A1 * | 7/2014 | Warner | A61M 5/1407 424/93.7 |
| 2014/0311253 | A1 * | 10/2014 | Iwasa | G01F 1/662 73/861.21 |
| 2015/0025485 | A1 * | 1/2015 | Luckemeyer | A61M 1/0025 604/319 |
| 2015/0110763 | A1 | 4/2015 | Leach | |
| 2015/0111195 | A1 | 4/2015 | Hamman et al. | |
| 2015/0111277 | A1 | 4/2015 | Hamman et al. | |
| 2016/0325039 | A1 | 11/2016 | Leach et al. | |

FOREIGN PATENT DOCUMENTS

| | | |
|---|---|---|
| WO | WO-2013049623 A1 | 4/2013 |
| WO | WO-2015061284 A1 | 4/2015 |
| WO | WO-2015061284 A1 | 4/2015 |
| WO | WO-2016160261 A1 | 10/2016 |

OTHER PUBLICATIONS

Invitation to Pay Additional Fees and Where Applicable Protest Fee dated Jan. 7, 2015 for PCT/US2014/061523 claiming benefit of U.S. Appl. No. 14/519,302, filed Oct. 21, 2014, U.S. Appl. No. 14/519,284, filed Oct. 21, 2014, U.S. Appl. No. 14/519,317, filed Oct. 21, 2014, claiming benefit of U.S. Appl. No. 62/011,992, filed Jun. 13, 2014, claiming priority of U.S. Appl. No. 61/979,695, filed Apr. 15, 2014, claiming priority of U.S. Appl. No. 61/893,555, filed Oct. 21, 2013.

Petersson, F., Aberg, L., Sward-Nilsson, A.M. and Laurell, T. Free Flow Acoustophoresis: Microfluidic-Based Mode of Particle and Cell Separation. Analytical Chemistry, vol. 79, No. 14 (Jul. 15, 2007) pp. 5117-5123.

Petersson, F., Nilsson, A., Jonsson, H. And Laurell. Carrier Medium Exchange through Ultrasonic Particle Switching in Microfluidic Channels. Analytical chemistry, vol. 77, No. 5 (Mar. 1, 2005) pp. 1216-1221.

Shi, J., Mao, X., Ahmed, D., Colletti, A., and Huang, T. Focusing mircroparticles in a microfluidic channel with standing surface acoustic waves (SSAW). Lab Chip. vol. 8 (2008) pp. 221-223.

"International Application Serial No. PCT/US2016/020594, International Search Report dated May 31, 2016", 5 pgs.

"International Application Serial No. PCT/US2016/020594, Written Opinion dated May 31, 2016", 6 pgs.

U.S. Appl. No. 15/217,635, filed Jul. 22, 2016, Cell Washing Using Acoustic Waves.

"International Application Serial No. PCT/US2016/020594, International Preliminary Report on Patentability dated Oct. 12, 2017", 8 pgs.

* cited by examiner

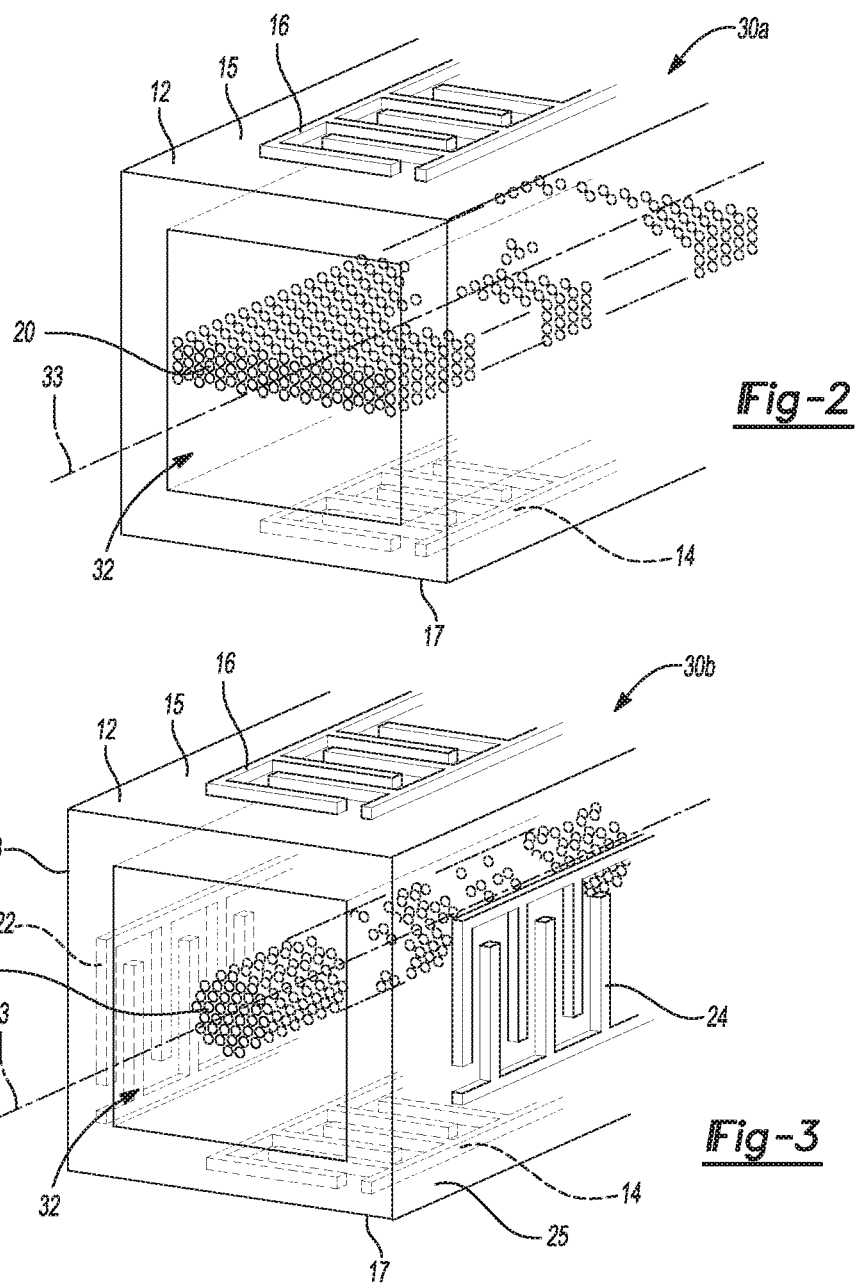

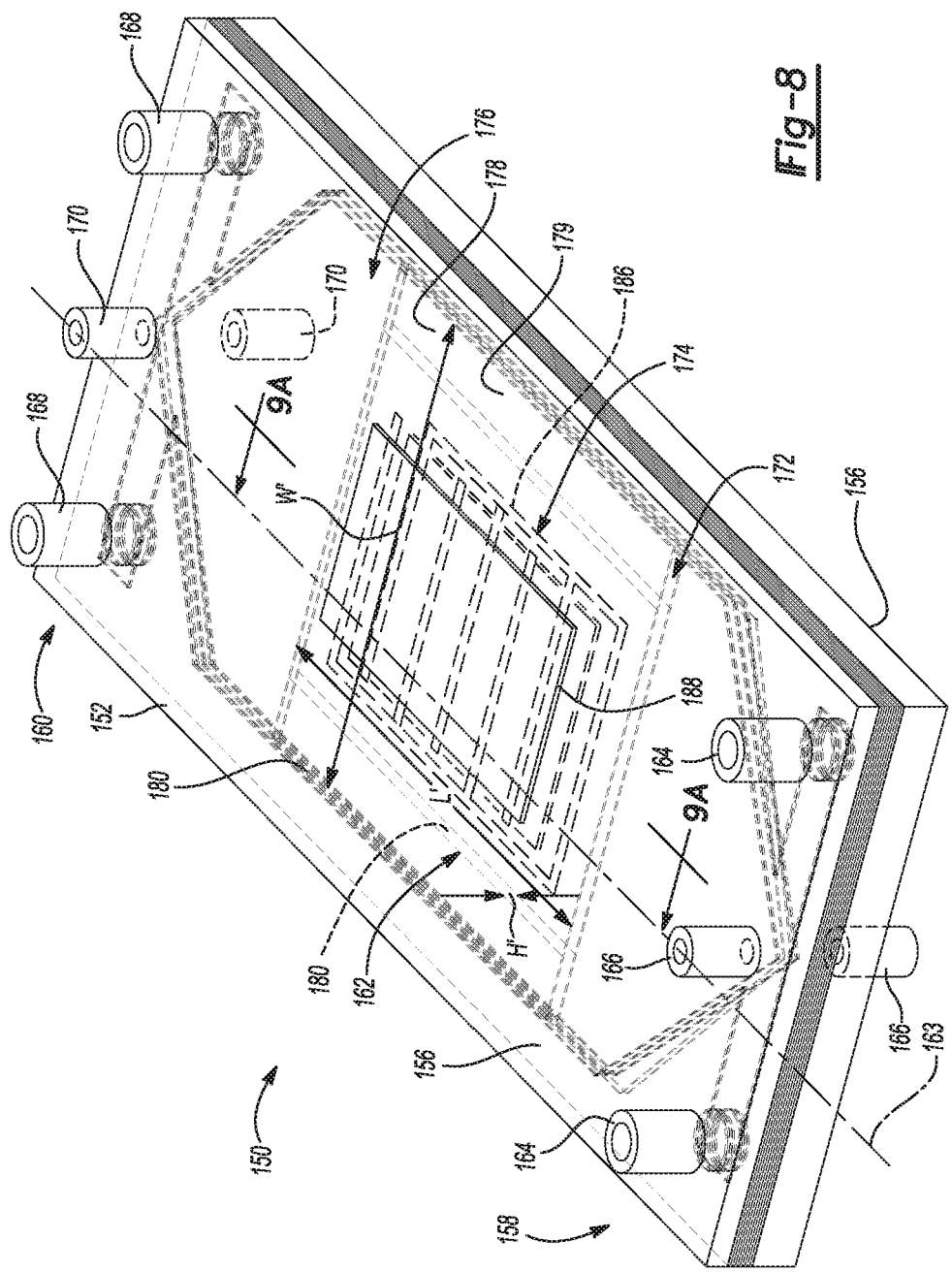

CELL WASHING DEVICE USING STANDING ACOUSTIC WAVES AND A PHANTOM MATERIAL

FIELD

The subject disclosure relates to separating components from a mixture (including a suspension), and particularly to separating a selected component in a high concentration and purity using a bulk acoustic wave.

BACKGROUND

This section provides background information related to the present disclosure which is not necessarily prior art.

Blood transfusions are used to treat many disorders and injuries, such as in the treatment of accident victims and during surgical procedures. According to current American Red Cross statistics, about 5 million people receive blood transfusions each year, in the United States alone. Thus, health care systems rely on the collection and distribution of blood. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during a medical procedure.

Donated blood is typically processed into components and then placed in storage until needed. When a subject is in need of a blood transfusion, a unit of blood is commonly removed from storage, rejuvenated, washed, and resuspended in an appropriate solution. In some instances, the red blood cells were lyophilized prior to storage, in which case they need to be resuspended, washed, and then resuspended again in an appropriate solution. The resuspended red blood cells are then transfused into the subject. In either scenario, washing the red blood cells is traditionally a tedious, time consuming and multistep process that requires a great deal of tubing, and the use of expensive centrifuges with rotating seals to separate the cells from the wash solution. Therefore, there remains a need to streamline and simplify the process for washing red blood cells prior to transfusion.

SUMMARY

This section provides a general summary of the disclosure, and is not a comprehensive disclosure of its full scope or all of its features.

The present technology provides a device for washing a composition comprising red blood cells. The device includes a body having a first surface, a second opposing surface, a first side, a second opposing side, a first end region, and a second end region. The body defines a channel that extends along a longitudinal axis from the first end region to the second end region. The channel includes a separation region. A first wave generator is coupled to the first surface of the device and either a second wave generator a reflective material or surface or layer is coupled to the second surface of the device. The separation region of the channel is positioned between the first wave generator and the second wave generator or first reflective material or surface or layer.

The present technology also provides a device for washing a multicomponent mixture. The device includes a body having a first surface and a second opposing surface, a first wave generator coupled to the first surface, and a wave component coupled to or forming the second surface. The wave component can be a second wave generator, a first reflective material, a first reflective surface, or a first reflective layer. The body defines a channel having a channel floor, and channel walls. The channel extends along a longitudinal axis from a first end region of the device to a second end region of the device. Also, the channel has a receiving region near the first end region, a collection region near the second end region, and a separation region between the receiving region and collection region. The separation region is positioned between the first wave generator and the wave component. The channel floor and walls are composed of a phantom material that mimics the acoustical properties of water.

Additionally, the present technology provides a system for washing a multicomponent mixture. The system includes a base unit and a disposable separation device. The base unit includes a first wave component and coupling members. The disposable separation device includes a body having a first surface, and a second opposing surface. The first surface includes a second wave component. The body defines a channel that extends along a longitudinal axis from a first end region of the device to a second end region of the device. The channel has a receiving region near the first end region, a collection region near the second end region and a separation region between the first and second wave components. The coupling members are configured to couple the disposable separation device to the base unit such that the separation region of the channel is positioned between the first wave component of the base unit and the second wave component of the disposable separation device.

The present technology further provides methods for washing a composition including cells. The method includes delivering the composition including cells and a wash material into a separation device having a body with a first surface having a first wave component and a second opposing surface having a second wave component. The body defines a separation channel extending from a first end region of the device to a second end region of the device. The channel has a receiving region, a separation region, and an collection region. The method also includes generating a standing acoustic wave with a pressure node located in the separation region of the channel. The standing acoustic wave is generated by the first and second wave components. Then, the method includes isolating cells by passing the composition including cells and wash material relative to the pressure node. The pressure node forces the cells to the collection region of the channel. The method additionally includes collecting the cells at an outlet of the device that is in fluid communication with the collection region of the channel.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a perspective illustration of cells flowing through a channel, the cells interacting with a single standing acoustic wave;

FIG. 3 is a perspective illustration of cells flowing through a channel, the cells interacting with a pair of orthogonal standing acoustic waves;

FIG. 8 is a perspective illustration of a device according to the present technology;

Corresponding reference numerals indicate corresponding parts throughout the several views of the drawings.

DETAILED DESCRIPTION

Figure 1A:
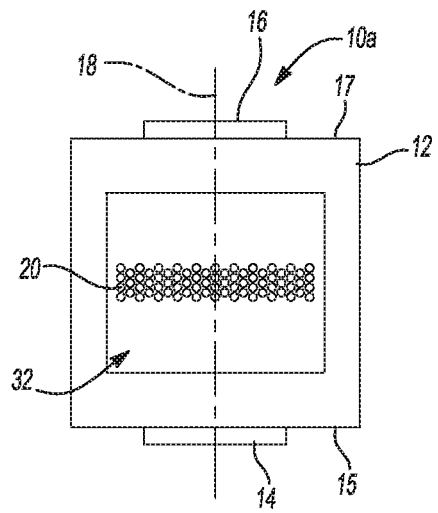
FIG. 1A is a schematic illustration of a cross section of a device configured to generate a standing acoustic wave.

Example embodiments will now be described more fully with reference to the accompanying drawings.

Although traditional methods for washing blood are effective, there remains a need to streamline the process for processing and washing blood. One possibility of streamlining the processes for processing and washing blood includes the use of standing waves, also referred to as stationary waves. Generally, standing waves can be formed from various mechanics, including interference between two waves. For example, two opposing waves can move towards one another in a medium and cause the formation of standing acoustic wave (SAW). When two waves are generated on opposite ends of a medium, they can interfere with each to generate a standing bulk acoustic wave (SBAW). Like other stationary waves, SBAWs are associated with both air displacement and pressure variation. Pressure variation can be used to manipulate particles in solution. As used herein, the term standing acoustic wave, or "SAW", includes the term standing bulk acoustic wave, or "SBAW". Therefore, devices and methods for separating a component from a mixture with the use of SAWs could streamline processes for processing multicomponent mixtures.

The present technology provides devices, systems, and methods for separating a component from a multicomponent mixture. The device, system, and methods include the use of SAWs that generate pressure nodes in separation channels. SAWs result when acoustic waves interfere with each other in opposite directions. For example, wave generators positioned on opposite sides of a piezoelectric material can generate SAWs, including SBAWs. Non-limiting examples of piezoelectric materials include quartz, quartz crystal, ceramic, ceramic composites, berlinite ($AlPO_4$), lead titanate ($PbTiO_3$), barium titanate ($BaTiO_3$), lead zirconate titanate ($Pb[Zr_xTi_{1-x}]O_3$, $0 \leq x \leq 1$; "PZT"), potassium niobate ($KNbO_3$), lithium niobate ($LiNbO_3$), lithium tantalate ($LiTaO_3$), sodium tungstate ($Na_2WO_3$), $Ba_2NaNb_5O_5$, $Pb_2KNb_5O_{15}$, zinc oxide (ZnO), sodium potassium niobate ($(K,Na)NbO_3$), bismuth ferrite ($BiFeO_3$), sodium niobate ($NaNbO_3$), bismuth titanate ($Bi4Ti_3O_{12}$, sodium bismuth titanate $Na_{0.5}Bi_{0.5}TiO_3$, and polymers, such as polyvinylidene fluoride (PVDF). A pressure node of a SAW forces, moves, or pushes a component in a mixture to a location within a separation channel based on the component's acoustical, physical, and mechanical properties.

A SAW can be generated between two wave generators. Wave generators include piezoelectric transducers and interdigitated transducers (IDTs). By positioning wave generators opposite each other on a substrate, an SAW can be generated when acoustic waves from each generator interfere with each other. Alternatively, an SAW can be generated by positioning a wave generator on one side of a substrate and positioning a reflective material or surface on a side of the substrate opposite the wave generator. When the wave generator produces an acoustic wave, the acoustic wave contacts the reflective surface and reflects back through the acoustic wave, toward the wave generator, thereby generating a SAW. In any embodiment described herein that includes a SAW, the SAW can be generated between two wave generators or between a wave generator and a reflective material, reflective surface, or reflective layer, unless provided otherwise. By adjusting the distance between the wave generators (or wave generator and reflective surface) and/or by adjusting the frequencies of the acoustic waves, the position of a pressure node associated with a SAW can be manipulated, located and controlled.

Devices

FIG. 1A shows a cross-sectional view of a device 10a comprising a substrate or device body 12, a first wave component 14, and a second wave component 16 positioned on opposite sides 15, 17 of the body 12, wherein the body 12 defines a channel 32 with a square cross-sectional geometry. The first wave component 14 and the second wave component 16 are individually either a wave generator or a reflective material or reflective surface or layer. However, when one of the wave components 14, 16 is a reflective material or reflective surface or layer, the other wave component 14, 16 is a wave generator. In various embodiments, the reflective material is a slide, layer or membrane composed of glass, polymer, plastic, metal, or ceramic. As non-limiting examples, the reflective material can be biaxially-oriented polyethylene terephthalate (boPET) polyester film (such as Mylar® brand BoPET commercialized by DuPont; Wilmington, Del.), glass mica, polymers, or a combination thereof. Alternatively, a side 15, 17 of the device body 12 can be composed of a reflective material so long as the opposite side 15, 17 comprises a wave generator. A SAW is generated between the first wave component 14 and the second wave component 16 along line 18. A pressure node associated with the SAW, which is located within the channel 32, forces a plurality of cells 20 into a plane perpendicular to the line 18.

Figure 1B:
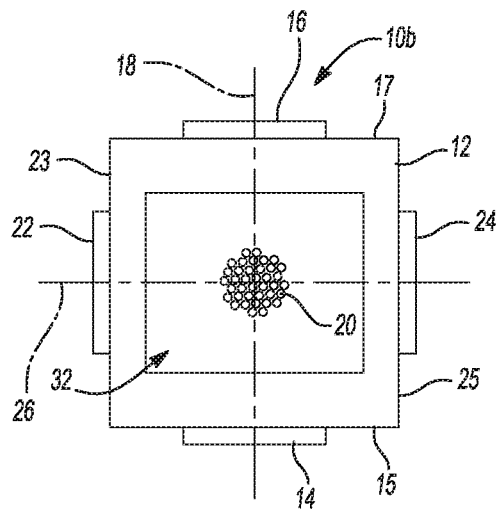
FIG. 1B is a schematic illustration of a cross section of a device configured to generate a pair of standing acoustic waves orthogonal to each other.

FIG. 1B shows a cross-sectional view of a device 10b, which is similar to device 10a. However, the device 10b further comprises a third wave component 22 and a fourth wave component 24 positioned on opposite sides 23, 25 of the body 12. The third wave component 22 and the fourth wave component 24 are individually either a wave generator or a reflective material or reflective surface or layer. However, when one of the wave components 22, 24 is a reflective material or reflective surface or layer, the other wave component 22, 24 is a wave generator. The third wave component 22 and the fourth wave component 24 are positioned orthogonal to the first wave component 14 and the second wave component 16 on sides 23, 25 of the body 12. A first SAW is generated between the first wave component 14 and the second wave component 16 along line 18 and a second SAW is generated between the third wave component 22 and the fourth wave component 24 along line 26 that is orthogonal to the first line 18, such that the second SAW is orthogonal to the first SAW. Pressure nodes associated with the SAWs interest with each other and interact with the plurality of cells 20 in orthogonal directions to force the cells 20 into a linear configuration, as shown more clearly in FIG. 3.

FIG. 2 provides a perspective view of a device 30a, which is similar to the device 10a. The device 30a comprises a substrate or device body 12, a first wave component 14, and a second wave component 16 positioned on opposing sides 15, 17 of the body 12. As shown in FIG. 2, the first and second wave components 14, 16 are wave generators. The device 30a comprises a longitudinal channel 32 with a square cross-sectional geometry that extends along a longitudinal axis 33. As shown in FIG. 2, the cells 20 are suspended in a plane that extends along the axis 33 and that is parallel to the wave components 14, 16 by a pressure node associated with a SAW generated by the first wave component 14 and the second wave component 16.

FIG. 3 provides a perspective view of a device 30b, which is similar to the device 10b. The device 30b comprises a substrate or device body 12, a first wave component 14 and a second wave component 16 positioned on opposing sides 15, 17 of the body 12, and a third wave component 22 and a fourth wave component 24 positioned on opposing sides 23, 25 of the body 12 that are orthogonal to the sides 15, 17 that include the first and second wave components 14, 17. Again, the device 30b comprises a longitudinal channel 32 with a square cross-sectional geometry that extends along the axis 33. As shown in FIG. 3, the cells 20 are suspended in a cylindrical line along the axis 33 of the channel 32 by a first pressure node associated with a first SAW generated by the first wave component 14 and the second wave component 16 and by a second pressure node associated with a second SAW generated by the third wave component 22 and the fourth wave component 24, wherein the second SAW is orthogonal to the first SAW.

Figure 1C:
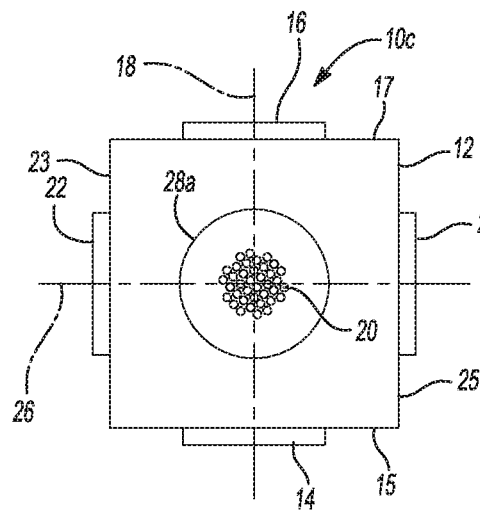
FIG. 1C is a schematic illustration of a cross section of device comprising a centered channel, the device configured to generate a pair of standing acoustic waves orthogonal to each other.
Figure 1D:
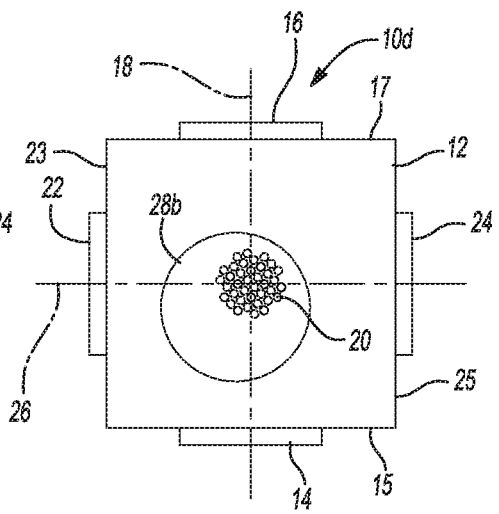
FIG. 1D is a schematic illustration of a cross section of device comprising an offset channel, the device configured to generate a pair of standing acoustic waves orthogonal to each other.

Referring now to FIG. 1C, a device 10c is shown, which is similar to device 10b. However, device 10c further comprises a channel 28a with a circular cross-sectional shape. Because the channel 28a is centered in the substrate 12, and because the wave components 14, 16, 22, 24 are centered on their respective sides of the substrate 12, the cells 20 are suspended in a line central to the channel 28a. As shown in FIG. 1D, a device 10d comprises a channel 28b, which is offset relative to the center of the substrate 12. However, the cells 20 are positioned in a line extending along a cross-sectional quadrant of the channel 28a because the pressure nodes intersect in that cross-sectional quadrant. In other words, the cells 20 are positioned based upon the node or nodes and not upon the positioning of the channel 28a, 28b, 32.

In various embodiments, the devices 10a, 10b, 10c, 10d shown in FIGS. 1A-1D are composed of a phantom material. As used herein, a "phantom material" is a material that mimics the acoustical properties of water. Therefore, an acoustic wave travels through phantom materials substantially as it would, such as with the same speed, through water. For example, sound travels through water at a rate of from about 1450 m/sec to about 1570 m/s. Similarly, sound travels through the phantom materials at a rate of from about 1200 m/s to about 1600 m/s, or at a rate of from about 1400 m/s to about 1500 m/s. Non-limiting examples of phantom materials include Solid Water® phantom material from CNMC Co. Inc. (Nashville, Tenn.), Virtual Water™ phantom material from CNMC Co. Inc., and Plastic Water® phantom material from Computerized Imaging Reference Systems, Inc. (Norfolk, Va.). Various plastics, acrylics, and glasses detrimentally affect how acoustic waves travel. Because phantom materials do not affect how an acoustic wave travels, separation devices with complex geometries, such as single chips or devices having multiple channels, can be generated. Additionally, the devices of the current technology may be multiplexed to reduce surface area and to increase efficiency.

The present technology provides devices, systems, and methods for washing a component of a multicomponent mixture. In various embodiments, the component is red blood cells and the multicomponent mixture comprises the red blood cells, at least a wash solution, and possibly other cell types, such as white blood cells, platelets, dead cells, or cell debris. For example, before transfusions, red blood cells are often rejuvenated with a rejuvenation solution, such as Rejuvesol® red blood cell processing solution commercialized by Citra Labs, LLC (Braintree, Mass.). After rejuvenation, rejuvenated red blood cells are washed with a wash solution, such as water, saline, dextrose, saline with 5% dextrose, phosphate buffered saline, and other wash liquids to remove excess rejuvenation solution from the red blood cells. Therefore, the rejuvenation solution and/or the wash solution need to be removed from the red blood cells prior to transfusion. Accordingly, the current technology separates red blood cells from a mixture of red blood cells, rejuvenation solution, wash solution, and optionally other types of cells, such as white blood cells, platelets, dead cells, and cell debris.

Figure 4:
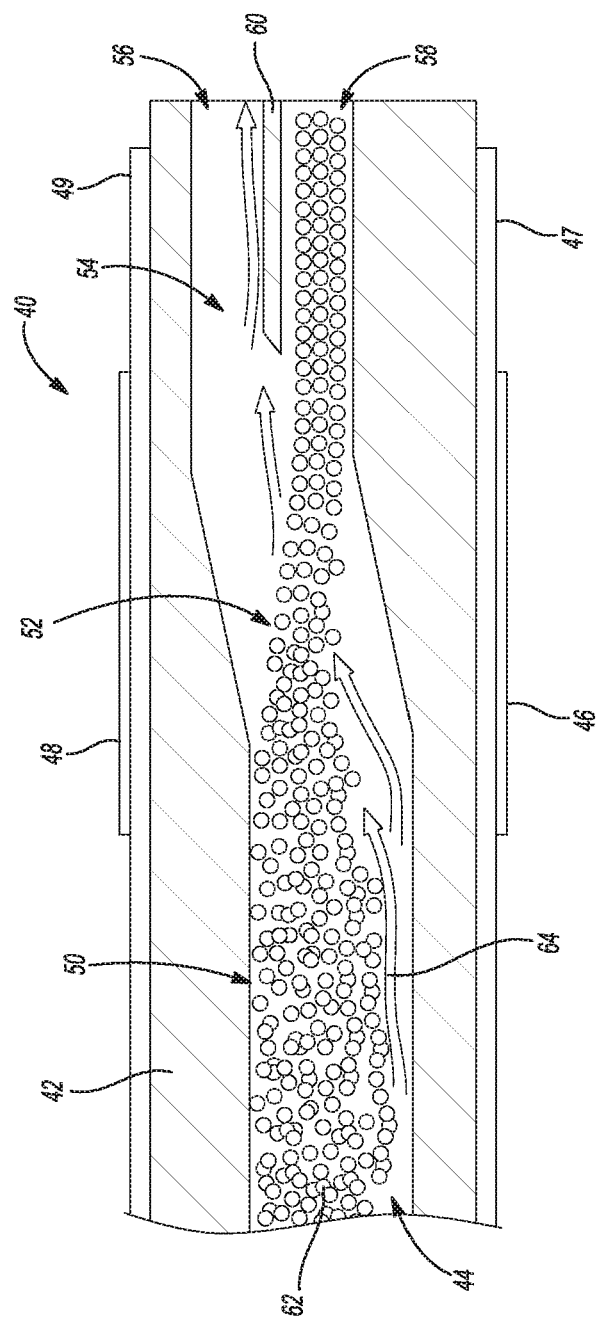
FIG. 4 is a cross-sectional representation of cells flowing through a device according to the present technology.

FIG. 4 shows a cross-section view of a device 40 for washing a multicomponent mixture comprising cells, such as, for example, red blood cells. The device 40 comprises a body 42 defining a channel 44, a first wave component 46 positioned on or near a first side 47 of the body 42 and a second wave component 48 positioned opposite to the first wave component 46 on or near a second side 49 of the body 42. The first wave component 46 and the second wave component 48 are individually either a wave generator or a reflective material or reflective surface or layer. However, when one of the wave components 46, 48 is a reflective material or reflective surface or layer, the other wave component 46, 48 is a wave generator. Therefore, at least one of the wave components 186, 188 is a wave generator. A SAW is generated between the first wave component 46 and the second wave component 48 such that a pressure node is located within the channel 44. The channel 44 comprises a first horizontal section 50, an second connecting section 52, and a third horizontal section 54, such that the first horizontal section 50 is offset from the second horizontal section 54. The third section 52 is bifurcated into a first collection channel 56 and a second collection channel 58 by a planar shelf 60 defined by the body 42. The wave components 46, 48 are positioned on the first side 47 and on the second side 49 of the body 42, respectively, which are parallel to the channel 44 at the connecting section 52 and the second horizontal section 54, such that the channel 44 is positioned between the first and second wave components 46, 48. When a multicomponent mixture comprising red blood cells 62 and a wash material 64 are introduced into the device 40, they mix at the first lower horizontal section 50. However, upon reaching the pressure node, the red blood cells 62 are forced into a plane at the connecting section 52. Simultaneously, the wash material, flow thereof represented by arrows 64, passes through the red blood cells 62, thereby washing the red blood cells 62. The red blood cells 62 are then collected from the second collection channel 58 and the wash material 64 and other waste is collected from the first collection channel 56. In other embodiments, the multicomponent mixture comprising red blood cells 62 and the wash material 62 are mixed prior to being introduced into the device 40.

Figure 5:
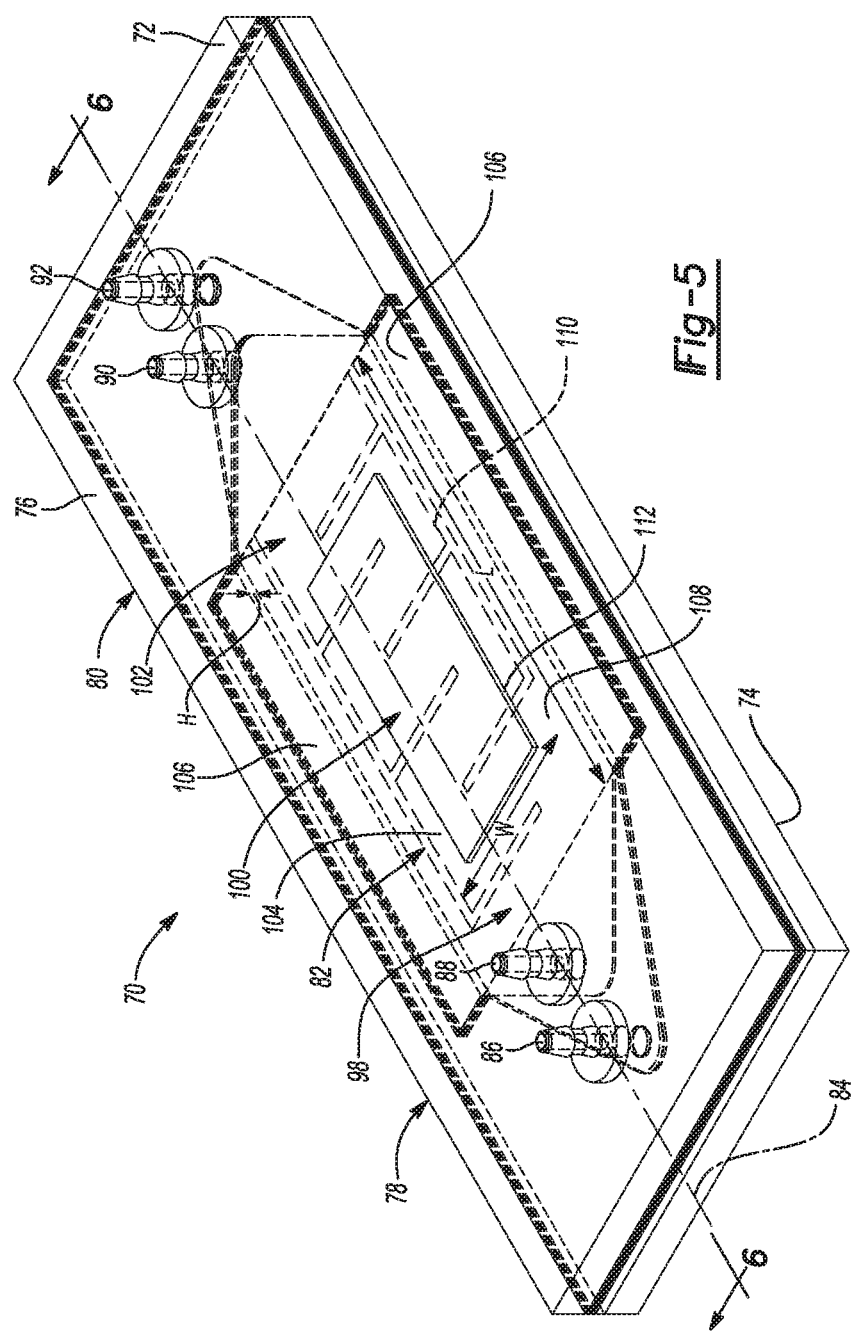
FIG. 5 is a perspective illustration of a device according to the present technology.
Figure 6A:
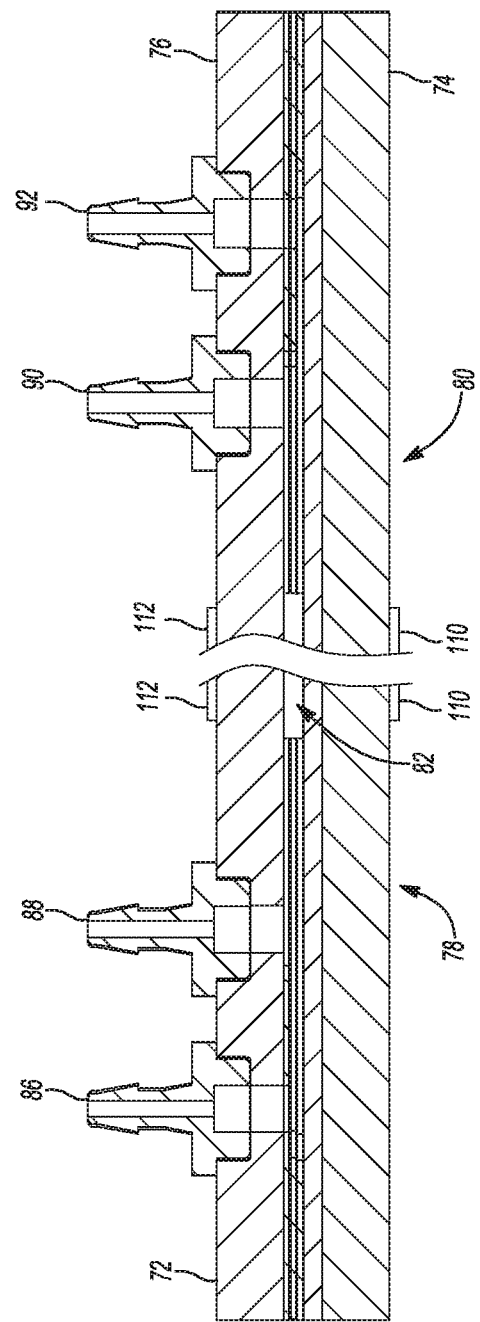
FIG. 6A is a cross-sectional perspective of the device of FIG. 5 taken along line 6A.
Figure 6B:
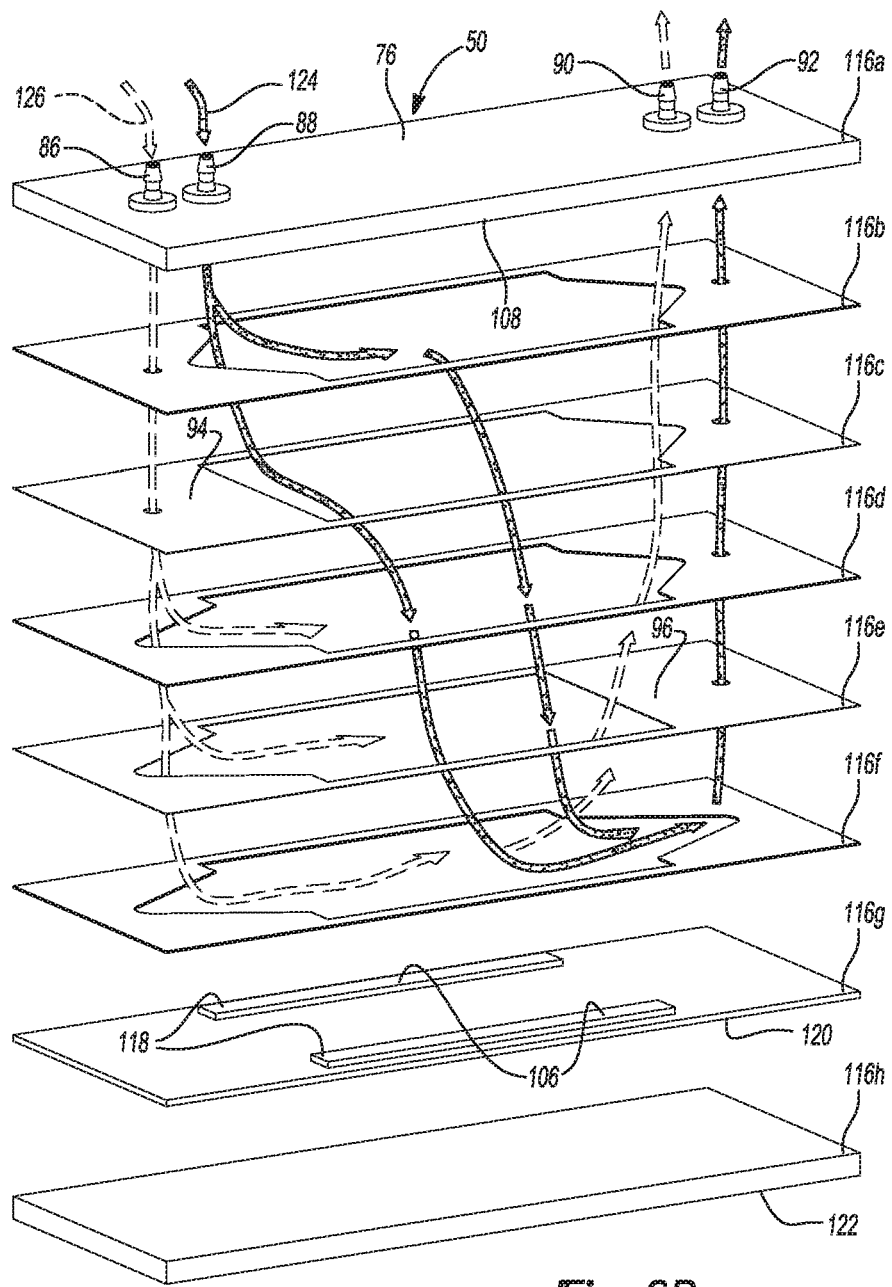
FIG. 6B is an exploded view of a plurality of layers that combine to form the device shown in FIGS. 5 and 6A.

With reference to FIG. 5, the present technology also provides a device 70 for washing a multicomponent mixture. The device 70 comprises a body 72 having a first surface 74, a second opposing surface 76, a first end region 78, and a second end region 80. The body 72 defines a channel 82 extending along a longitudinal axis 84 from the first end region 78 to the second end region 80. The device 70 further comprises a first inlet 86, a second inlet 88, a first outlet 90, and a second outlet 92, all in fluid communication with the channel 82. FIG. 6A is an exploded, cross-sectional perspective of the device 70 taken along line 6A of FIG. 5. when the device 70 is generated by stacking a plurality of layers together as shown in FIG. 6B. As shown in FIGS. 6A and 6B, the channel 82 is bifurcated at the first end region 78 by a first planar shelf 94 defined by the body 72, which keeps components that are introduced into the device 70 through the inlets 86, 88 separate. However, in some embodiments (not shown) there is only one inlet and no shelf to separate components. Also, the channel 82 is bifurcated at the second end region 80 by a second planar shelf 96 defined by the body 72, which keeps the components separated for collection through the outlets 90, 92 by way of a first collection channel 97 and a second collection channel 99, respectively.

The channel 82 of the device 70 includes a receiving or mixing region 98 near the first end region 78, a collection region 102 near the second end region 80, and a separation region 100 there between. Additionally, the channel 82 comprises a channel floor 104, two side walls 106 that extend longitudinally along the axis 84, and a channel ceiling 108. In various embodiments, the channel floor 104 and sides 106 are composed of a phantom material as described above. In various embodiments, at least the separation region 100 of the channel 82 has a rectangular cross-sectional geometry. Additionally, the separation region 100 of the channel 82 has a length L, a width W, and a height H that results in passing a large volume through the device. In various embodiments, the length L is greater than about 20 mm or greater than about 100 mm. In other embodiments, the length L is from about 10 mm to about 100 mm, or from about 25 mm to about 75. In yet other embodiments, the length L is about 10 mm, about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, or about 100 mm. In various embodiments, the width W is greater than about 5 mm, or greater than about 50 mm. In other embodiments, the width W is from about 5 mm to about 50 mm, or from about 20 mm to about 40 mm. In yet other embodiments, the width W is about 5 mm, about 10 mm, about 15 mm, about 20 mm, about 25 mm, about 30 mm, about 35 mm, about 40 mm, about 45 mm, or about 50 mm. In various embodiments, the height H is greater than about 0.5 mm, or greater than about 3 mm. In other embodiments, the height H is from about 0.5 mm to about 3 mm. In yet other embodiments, the height H is about 0.5 mm, about 1 mm, about 1.5 mm, about 2 mm, about 2.5 mm, or about 3 mm. The dimensions of the channel 82 allow for a high throughput of a mixture to be washed. Therefore, the device 70 can process blood compositions, mixtures, or suspensions at a rate of about 10 mL/min to about 30 mL/min, or at a rate from about 20 mL/min to about 25 mL/min. In one embodiment, the device 70 processes blood compositions, mixtures, or suspensions at a rate of about 22.5 mL/min. Accordingly, a unit of blood, having a volume of from about 400 mL to about 500 mL, combined with from about 0.5 L to about 3 L of wash solution can be processed in from about 30 min to about 350 min. In one embodiment, the device 70 can process a volume of 450 mL in about 20 min. However, the device 70 can accommodate and process a volume of from about 1 mL to about 20 L, wherein about 20 L can be processed in about 12 hrs, in about 13 hours, or in about 14 hrs.

Additionally, the device 70 comprises a first wave component 110 positioned adjacent and parallel to the channel 82 and a second wave component 112 positioned adjacent and parallel to the channel 82, such that the channel 82 is positioned between the first and second wave components 110, 112. In various embodiments, the separating region 100 of the channel 82 is positioned between the first and second wave components 110, 112. Unless described otherwise, the first wave component 110 and the second wave component 112 are individually either a wave generator or a reflective material or reflective surface or layer. However, when one of the wave components 110, 112 is a reflective material or reflective surface or layer, the other wave component 110, 112 is a wave generator. In embodiments where the second wave component 112 is a reflective surface, the reflective surface can be the second surface 76 of the device 70, or it can be a reflective film, sheet, slide, or membrane coupled to the second surface 76. As discussed further below, in some embodiments the first wave component 110 is an electrical contact that couples to a wave generator on a base unit. Therefore, when the first wave component 110 is a wave generator or an electrical contact, the second wave component 112 is either a second wave generator or a reflective surface or layer or material. When the device 70 is activated, a SAW is generated between the first wave component 110 and the second wave component 112, whereby a pressure node 114 (see FIG. 7B) associated with the SAW is located within the separation region 100 of the channel 82. In various embodiments, the SAW is generated from the wave components 86, 88 operating at a low frequency range of from about 300 kHz to about 1000 kHz, or from about 400 kHz to about 600 kHz, or from about 450 kHz to about 500 kHz, in order to isolate components from a multicomponent mixture in the channel 62 with such a large volume. Even though this low frequency range results in a low pressure gradient, surprisingly, component isolation is achieved. In other embodiments, not shown in FIG. 4, the device 70 further comprises third and fourth wave components as or on opposing sides of the device 70 such that the third and fourth wave components generate a second SAW orthogonal to the SAW generated by the first and second wave components 110, 112, wherein the second SAW provides a second pressure node located in the separation region 100 of the channel 82.

The device 70 can be manufactured by any means known in the art, including, for example, injection molding, compression molding, or 3-dimensional printing (3-D printing). In some embodiments, as shown in FIG. 6B, the device 70 is manufactured by stacking together a plurality of layers 116a-116h, wherein each layers is bonded to an adjacent layer with an adhesive. With the optional exception described below in regard to the layer 116g, the layers 116a-116h are composed of any material known in the art. Non-limiting examples of materials for the layers 116a-116h include plastics, such as polyethylene terephthalate (PET) acrylics, such as poly(methyl methacrylate) (PMMA), and glasses. Combining the layers 116a-116h results in the device 70 with the cross-sectional geometry shown in FIG. 6A. The layer 116g has two longitudinal protrusions 118 that form the two side walls 106 of the channel 82. In various embodiments, the layer 116g is composed of a phantom material that mimics how acoustic waves travel through water to provide the device 70 with the channel 82 having phantom side walls 106 and a phantom floor 104. In some embodiments, not shown in FIG. 6A or 6B, the first wave component 110 is coupled to a bottom surface 120 of the layer 116g and the layer below it, layer 116h, is optional. In other embodiments, the first wave component 110 is coupled to a bottom surface 122 of the layer 116h. A first layer 116a can either be composed of a reflective material or the second wave component 112 can be coupled to a surface 76 of the layer 116a. Moreover, the first layer 116a can be composed of a phantom material in various embodiments.

Figure 7A:
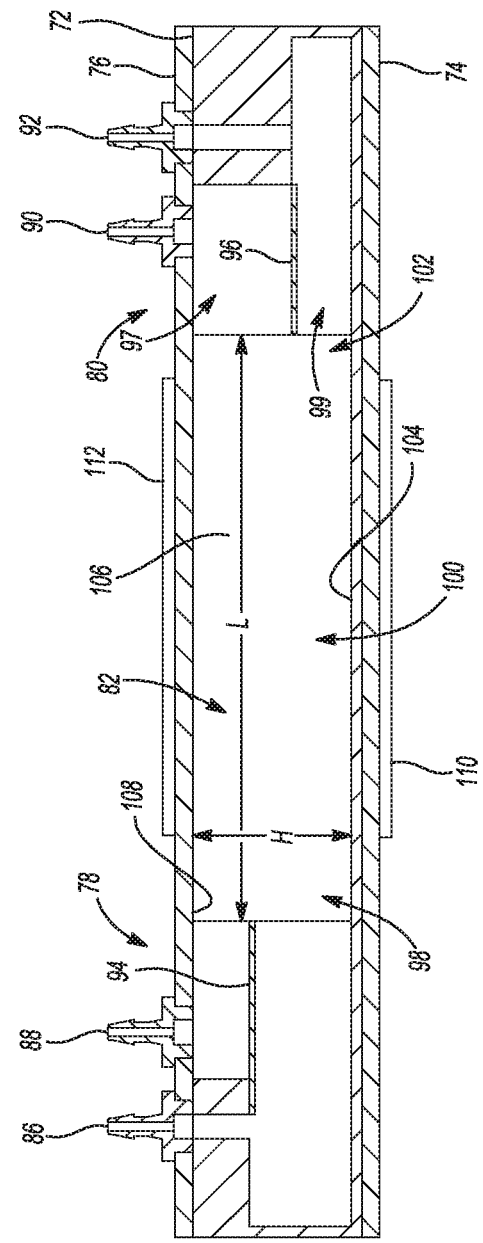
FIG. 7A is a cross-section perspective of the device of FIG. 5 that does not include a plurality of layers.

FIG. 7 is a cross-sectional illustration of the device 70 when the device 70 is manufactured by a means other than by stacking together a plurality of layers, such as by injection molding, compression molding, or 3-D printing. The components of FIG. 7 are the same as those shown in FIGS. 6A and 6B, but the dimensions may be slightly different.

Figure 7B:
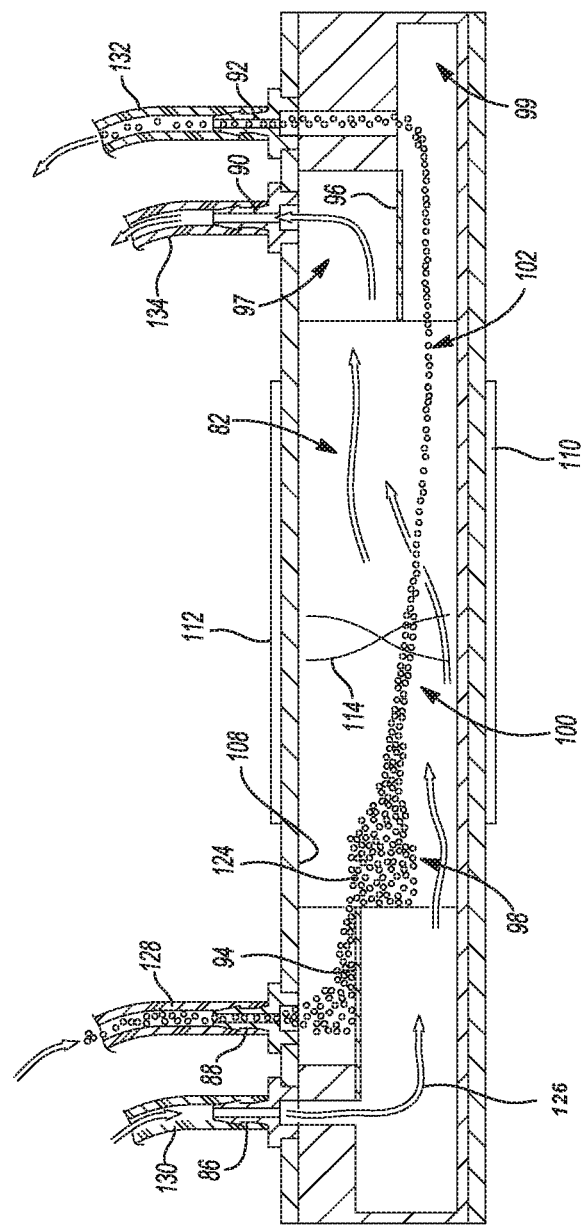
FIG. 7B is a cross-section perspective of the device of FIG. 7A, wherein cells and wash material are flowing through the device.

With reference to FIGS. 5-7B, the device 70 is configured to wash a multicomponent mixture. As described above, in various embodiments the multicomponent mixture comprises red blood cells 124 or red blood cells 124 and a rejuvenation solution. The multicomponent mixture is introduced to the device 70 through a first conduit coupled to an inlet 86, 88. As shown in FIG. 7B, a first conduit 128 is coupled to the second inlet 88. Likewise, a wash material 126 is introduced to the device 70 through a second conduit coupled to the inlet 86, 88 that is not coupled to the first conduit 128. As shown in FIG. 7, a second conduit 130 is coupled to the first inlet 86. Flow of the multicomponent mixture comprising red blood cells 124 and the wash material 126 can be established, by pumps, such as peristaltic pumps, optionally coupled to pulse dampeners or pulse suppressors. Examples of suitable pumps, pulse dampeners, and pulse suppressors that can be used for any embodiments provided herein are described in U.S. patent application Ser. No. 14/519,302, filed on Oct. 21, 2014, to Hamman et al., which is incorporated herein by reference. Upon entry into the device 70, the multicomponent mixture comprising red blood cells 124 and the wash material 126 are mixed together at the receiving or mixing region 98 of the channel 82. In other embodiments, the multicomponent mixture and washing material are combined prior to being introduced into the device 70. In such embodiments, the device 70 may have a single input, as described above or the multicomponent mixture and wash material can be delivered into the device by either inlet 86, 88 of the device 70. Referring again to FIGS. 5-7B, as the multicomponent mixture comprising red blood cells 124 and the wash material 126 flow through the channel 82, they interact with a pressure node 114, generated by the wave components 110, 112, in the separation region 100 of the channel 82. The pressure node 114 pushes, forces, isolates, or moves a component of the multicomponent mixture, such as the red blood cells 124, adjacent to the shelf 96 and into the second collection channel 99 while the remainder of the multicomponent mixture and wash material 126 flow to the first collection channel 97. The shelf 96 is thin and rigid so as to minimize turbulence within the channel 82. The component pushed, forced, isolated, or moved to the second collection channel 99 is collected through a third conduit 132 coupled to the second outlet 92 and the remaining materials are collected through a fourth conduit 134 coupled to the first outlet 90.

Although FIGS. 7 and 8 show an isolated component flowing to the second collection channel 99, in other embodiments the pressure node is located within the channel 82 such that the component is forced to the first collection channel 97. In such embodiments, the isolated component is collected through the first outlet 90 and the remaining materials are collected through the second outlet 92.

Figure 9A:
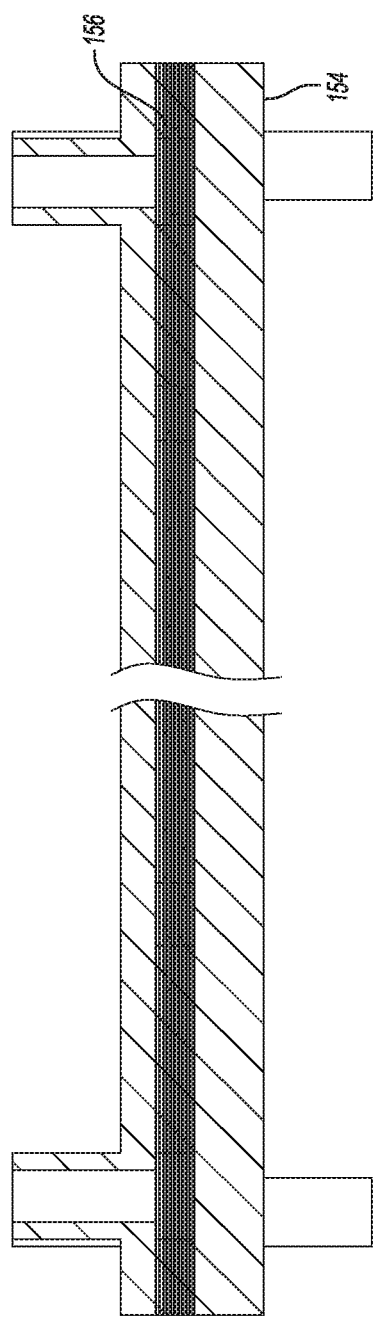
FIG. 9A is a cross-sectional perspective of the device of FIG. 8 taken along line 9A.
Figure 9B:
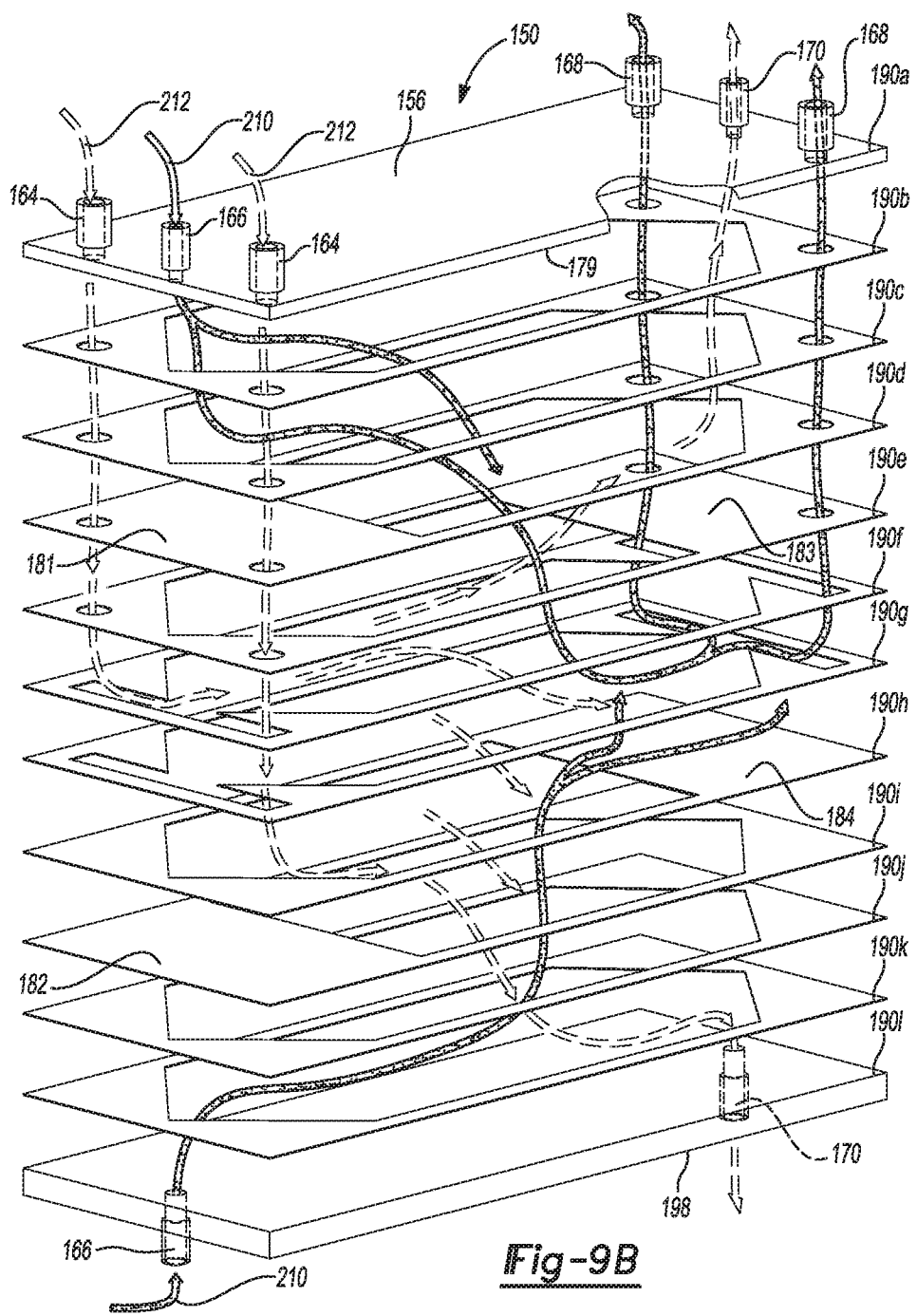
FIG. 9B is an exploded view of a plurality of layers that combine to form the device shown in FIGS. 8 and 9A.
Figure 10:
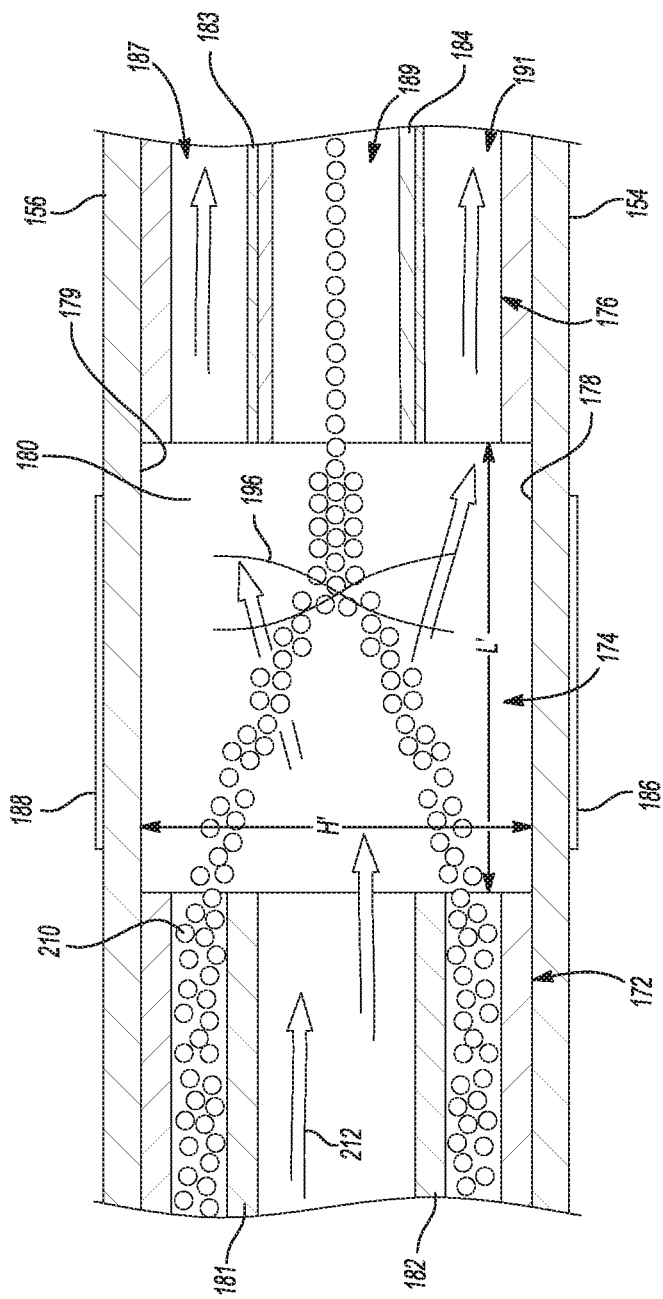
FIG. 10 is a cross-section perspective of the device of FIG. 8 that does not include a plurality of layers.

With reference to FIGS. 8-10, the present technology provides another device 150 for washing a multicomponent mixture. The device 150 comprises a body 152 having a first surface 154, a second opposing surface 156, a first end region 158, and a second end region 160. The body 152 defines a channel 162 extending along a longitudinal axis 163 from the first end region 158 to the second end region 160. The device 150 further comprises a first pair of inlets 164, a second pair of inlets 166, a first pair of outlets 168, and a second pair of outlets 170, all in fluid communication with the channel 162. FIG. 10 is an exploded cross-sectional perspective of the device 150 taken along line 9A of FIG. 8 when the device 150 is generated by stacking a plurality of layers together as shown in FIG. 9B. As shown in FIGS. 9A and 9B, the channel 162 is trifurcated at the first end region 158 by a first shelf 181 defined by the body 152 and a second shelf 182 defined by the body 152, which keeps components that are introduced into the device 150 through the pairs of inlets 164, 166 separate. Also, the channel 162 is trifurcated at the second end region 160 into a first collection channel 187, a second collection channel 189, and a third collection channel 191 by a third shelf 183 defined by the body 152 and fourth shelf 184 defined by the body 152, wherein the first collection channel 187 is located between the second surface 156 and the third shelf 183, the second collection 189 channel is located between the third and fourth shelves 183, 184, and the third collection channel 191 is located between the fourth shelf 184 and the first surface 154. The collection channels 187, 189, 191, keep the components separated for collection through the pairs of outlets 168, 170, such that the second collection channel 189 is in fluid communication with the first pair of outlets 168 and the first and third collection channels 187, 191 are in fluid communication with the second pair of outlets 170.

The channel 162 of the device 150 includes a receiving or mixing region 172 near the first end region 158, a collection region 176 near the second end region 160, and a separation region 174 there between. Additionally, the channel comprises a channel floor 178, two side walls 180 that extend longitudinally along the axis 163, and a channel ceiling 179. In various embodiments, the channel floor 178 and sides 180 are composed of a phantom material as described above. In various embodiments, at least the separation region 174 of the channel 162 has a rectangular cross-sectional geometry. Additionally, the separation region 174 of the channel 162 has a length L', a width W', and a height H' that results in passing a large volume through the device 150. In various embodiments, the length L' is greater than about 20 mm or greater than about 100 mm. In other embodiments, the length L' is from about 10 mm to about 100 mm, or from about 25 mm to about 75. In yet other embodiments, the length L' is about 10 mm, about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, or about 100 mm. In various embodiments, the width W' is greater than about 5 mm, or greater than about 50 mm. In other embodiments, the width W' is from about 5 mm to about 50 mm, or from about 20 mm to about 40 mm. In yet other embodiments, the width W' is about 5 mm, about 10 mm, about 15 mm, about 20 mm, about 25 mm, about 30 mm, about 35 mm, about 40 mm, about 45 mm, or about 50 mm. In various embodiments, the height H' is greater than about 0.5 mm, or greater than about 3 mm. In other embodiments, the height H' is from about 0.5 mm to about 3 mm. In yet other embodiments, the height H' is about 0.5 mm, about 1 mm, about 1.5 mm, about 2 mm, about 2.5 mm, or about 3 mm. The dimensions of the channel 62 allow for a high throughput of a mixture to be washed. Therefore, the device 150 can process blood compositions, mixtures, or suspensions at a rate of about 10 mL/min to about 30 mL/min, or at a rate from about 20 mL/min to about 25 mL/min. In one embodiment, the device 150 processes blood compositions, mixtures, or suspensions at a rate of about 22.5 mL/min. Accordingly, a unit of blood, having a volume of from about 400 mL to about 500 mL, combined with from about 0.5 L to about 3 L of wash solution can be processed in from about 30 min to about 350 min. In one embodiment, the device 150 can process a volume of 450 mL in about 20 min. However, the device 150 can accommodate and process a volume of from about 1 mL to about 20 L, wherein about 20 L can be processed in about 12 hrs, in about 13 hours, or in about 14 hrs.

Additionally, the device 150 comprises a first wave component 186 positioned adjacent to the channel 162 on or near the first side 154 of the device 150 and a second wave component 188 positioned adjacent to the channel 162 on or near the second side 156 of the device 150 such that the channel 162 is positioned between the first and second wave components 186, 188. In various embodiments, the separation region 174 of the channel 162 is positioned between the first and second wave components 186, 188. Unless described otherwise, the first wave component 186 and the second wave component 188 are individually either a wave generator or a reflective material or reflective surface. However, when one of the wave components 186, 188 is a reflective material or reflective surface, the other wave component 186, 188 is a wave generator. Therefore, at least one of the wave components 186, 188 is a wave generator. In embodiments where the second wave component 188 is a reflective surface, the reflective surface can be the second surface 156 of the device 150, or it can be a reflective film, sheet, slide, or membrane. As discussed further below, in some embodiments the first wave component 186 is an electrical contact that couples to a wave generator on a base unit. Therefore, when the first wave component 186 is a wave generator or an electrical contact, the second wave component 188 is either a second wave generator or a reflective surface or material. When the device 150 is activated, a SAW is generated between the first wave component 186 and the second wave component 188, whereby a pressure node 196 (see FIG. 10) associated with the SAW is positioned within the separation region 174 of the channel 162. In various embodiments, the SAW is generated from the wave components 186, 188 operating at a low frequency range of from about 300 kHz to about 1000 kHz, or from about 400 kHz to about 600 kHz, or from about 450 kHz to about 500 kHz, in order to isolate components from a multicomponent mixture in the channel 162 with such a large volume. Even though this low frequency range results in a low pressure gradient, surprisingly, component isolation is achieved. In other embodiments, not shown in FIG. 8, the device 150 further comprises third and fourth wave components as or on opposing sides of the device 150 such that the third and fourth wave components generate a second SAW orthogonal to the SAW generated by the first and second wave components 186, 188, wherein the second SAW provides a second pressure node located in the separation region 174 of the channel 162.

Figure 11:
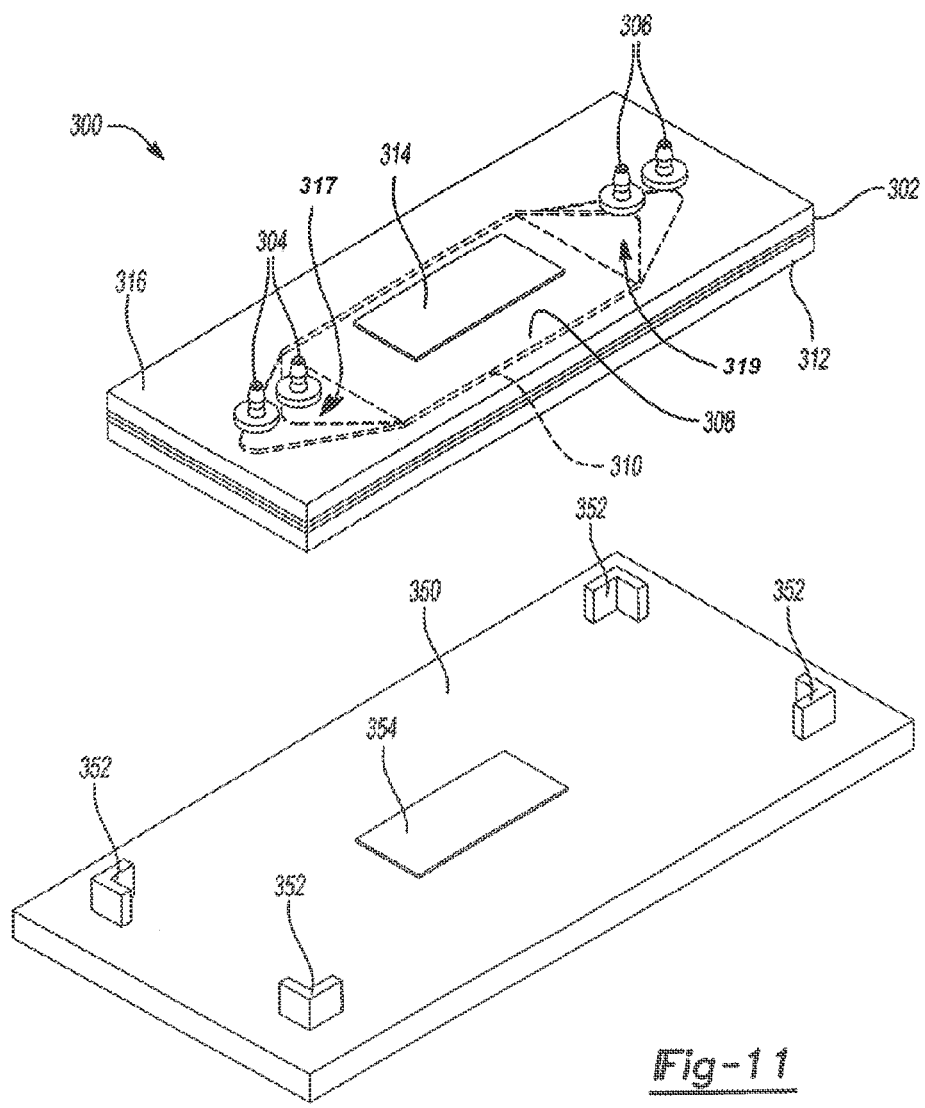
FIG. 11 is a schematic illustration of a system for washing multicomponent mixtures according to the present technology.

The device 150 can be manufactured by any means known in the art, including, for example, injection molding, compression molding, or 3-dimensional printing (3-D printing). In some embodiments, as shown in FIG. 11, the device 150 is manufactured by stacking together a plurality of layers 190a-190l, wherein each layers is bonded to an adjacent layer with an adhesive. With the optional exception described below in regard to a phantom layer, the layers 190a-190l are composed of any material known in the art. Non-limiting examples of materials for the layers 190a-190l include plastics, such as polyethylene terephthalate (PET) acrylics, such as poly(methyl methacrylate) (PMMA), and glasses. Combining the layers 190a-190l results in the device 150 with the cross-sectional geometry shown in FIG. 10. Optionally, an optional layer equivalent to layer 90g of FIG. 7, but configured to provide communication between layer 190k and the second input 166 and second output 170, is positioned between layer 190k and 190l and has two longitudinal protrusions that form the two side walls 180 of the channel 162. In various embodiments, the optional layer is composed of a phantom material that mimics how acoustic waves travel through water to results in the device 150 with the channel 162 having phantom side walls 180 and a phantom floor 178. In some embodiments, not shown in FIG. 11, the first wave component 186 is coupled to a bottom surface of the optional layer. In other embodiments, the first wave component 186 is coupled to a bottom surface 198 of the layer 190l. In yet other embodiments, layer 190l is composed of a phantom material and comprises two longitudinal protrusions that form the two side wall 180 of the channel 162. In such embodiments, the first wave component 186 is coupled to the bottom surface 198 of the layer 190l. A first layer 190a can either be composed of a reflective material or the second wave component 188 can be coupled to the second surface 156 of the layer 190a. Moreover, the first layer 190a is composed of a phantom material in various embodiments.

FIG. 10 is a cross-sectional illustration of the device 150 when the device 150 is manufactured by a means other than by stacking together a plurality of layers, such as by injection molding, compression molding, or 3-D printing. The components of FIG. 10 are the same as those shown in FIGS. 9A and 9B, but the dimensions may be slightly different.

With reference to FIGS. 8-10, the device 150 is configured to wash a multicomponent mixture. As described above, in various embodiments the multicomponent mixture comprises red blood cells 210 or red blood cells 210 and a rejuvenation solution. The multicomponent mixture comprising red blood cells 210 is introduced to the device 150 through a pair of first conduits coupled to the pair of second inlets 166. Likewise, a wash material 212 is introduced to the device 150 through a pair of second conduits coupled to the pair of first inlets 164. Flow of the multicomponent mixture 210 and the wash material 212 can be established, by pumps, such as peristaltic pumps, optionally coupled to pulse dampeners or pulse suppressors, as described above. Upon entry into the device 150, the multicomponent mixture 210 and the wash material 212 are mixed together at the receiving or mixing region 172 of the channel 162. In other embodiments, the multicomponent mixture comprising red blood cells 210 and the washing material 212 are combined prior to be introduced into the device 150 to generate a pre-mixed composition. In such embodiments, the device 150 may have a single input, as described above, or the pre-mixed composition can be delivered into the device 150 by any inlet or combination of inlets 164, 166. Referring again to FIGS. 8-10, as the multicomponent mixture comprising red blood cells 210 and the wash material 212 flow through the channel 162, they interact with a pressure node 196, generated by the wave components 186, 188, in the separation region 174 of the channel 162. The pressure node 196 pushes, forces, isolates, or moves a component of the multicomponent mixture, such as red blood cells, between the third and fourth shelves 183, 184 and into the second collection channel 189 while the remainder of the multicomponent mixture and wash material flow into the first and third collection channels 187, 191. The third and fourth shelves 183, 184 are thin and rigid so as to minimize turbulence within the channel 162. The component pushed, forced, isolated, or moved into the second collection channel 180 is collected through a third pair of conduits coupled to the first pair of outlets 168 and the remaining materials are collected through a fourth pair of conduits coupled to the second pair of outlets 170.

Systems

As shown in FIG. 11, the present technology further provides a system 300 for washing multicomponent mixtures. The system comprises a disposable separation device 302 and base unit 350. Any separation device described herein, including the device 70 of FIG. 5 and the device 150 of FIG. 8 can be used as the separation device 302. In general, the separation device 302 comprises inlets 304, outlets 306, a channel 308, an optional first wave component 310 coupled to a first surface 312, and a second wave component 314 coupled to a second opposing surface 316, wherein the inlets 304 are in fluid communication with a first end of the channel 317 and the outlets 306 are in fluid communication with a second end of the channel 319. The optional first wave component 310 can be a wave generator. The second wave component 314 can be a wave generator or a reflective material or surface or layer.

The base unit 350 comprises at least one of a plurality of coupling members 352 and a third wave component 354. The coupling members can be any coupling members known in the art. Non-limiting examples of connecting members include snaps, clips, clasps, screws, adhesives, fasteners, etc. The third wave component 354 is either a wave generator or an electrical contact. In embodiments where the first wave component 310 of the disposable separation device 302 is a wave generator, the third wave component 354 is an electrical contact. In one embodiment the disposable separation device 302 comprises a first wave component 310, which is a wave generator. In such embodiments, the third wave component 354 of the base unit 350 is an electrical contact. The coupling members 352 are then configured to couple and hold the disposable separation device 302 to the base unit 350 such that the wave generator of the disposable separation device 302 contacts and communicates with the electrical contact. In another embodiment, the disposable device 302 does not comprise a first wave component 310. In this embodiment, the third wave component 354 of the base unit 350 is a wave generator. The snaps 352 are then configured to snap the disposable separation device 302 to the base unit 350 such that the separation channel 308 is positioned between the wave generator on the base unit 350 and the second wave component 314 of the disposable separation device 302. Nonetheless, in all embodiments a SAW is generated in the disposable separation device 302 with power provided by the base unit 350.

The disposable separation device 302 can be prepackaged and sterilized. When ready for use, the disposable separation device 302 is removed from the packaging and snapped onto the base unit 350. A wash material is then pumped through the device and the base unit is activated to generate an SAW. A multicomponent mixture, such as a red blood cell composition, is then pumped through the separation device 302, wherein the blood is washed and separated from undesired components.

Method

The present technology also provides a method for washing a composition comprising cells. The method comprises delivering, such as by pumping or flowing, a composition comprising cells and a wash material into a separation device comprising a separation channel having a receiving or mixing region, a separation region and a collection region. In various embodiments, the composition comprising cells is a composition comprising red blood cells. The composition may also comprise materials to be washed away from the cells, including other cell types, dead cells, cell debris, rejuvenation solution, or combinations thereof. The wash material is selected from the group consisting of water, saline, dextrose, saline with 5% dextrose, and phosphate buffered saline. The separation device can be any separation device described above.

The method also comprises mixing the composition comprising cells with the wash material. Mixing occurs when the composition comprising cells contacts the wash material in the receiving or mixing region of the channel. Alternatively, the composition comprising cells can be mixed with the wash material outside of the device to generate a pre-mixed composition. In such embodiments, the pre-mixed composition is delivered into the separation device. Then, the method comprises isolating or separating a component from the composition comprising cells. The component can be a desired type of cell, such as, for example, red blood cells. Isolating or separating a component comprises passing, such as by pumping or flowing, the composition comprising cells and the wash material relative to a pressure node generated by a SAW, wherein a pressure node associated with the SAW is located within the separation region of the channel. The SAW is generated by wave components operating at a frequency range of from about 300 kHz to about 1000 kHz.

After the component is isolated or separated, the method comprises collecting the component at an outlet of the device that is in fluid communication with the collection region of the channel. In embodiments where the composition comprising cells is a composition comprising red blood cells, the red blood cells can be washed and isolated by this method, and then transfused into a human or non-human subject in need thereof.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for washing a composition comprising red blood cells, the device comprising:
   a body having a first surface, a second opposing surface, a first side, a second opposing side, a first end, and a second end, the body defining a channel extending along a longitudinal axis from the first end to the second end, wherein the channel comprises a separation region and a mixing region, the body further including a first planar shelf proximate the first end and arranged to isolate a first inflow stream from a second inflow stream prior to the first inflow stream and the second inflow stream entering the mixing region;
   a first sidewall located along the first side within the channel and extending along the longitudinal axis;
   a first protrusion extending from the first surface and adjacent to the first sidewall, the first protrusion extending a length of the first sidewall;
   a second sidewall located along the second side within the channel and extending along the longitudinal axis, the first sidewall and the second sidewall being a phantom material;
   a second protrusion extending from the first surface and adjacent to the second sidewall, the second protrusion extending a length of the second sidewall;
   a first wave component coupled to the first surface; and
   a second wave component coupled to the second surface, wherein the separation region of the channel is positioned between the first wave component and the second wave component, and wherein the first wave component and second wave component are configured to generate a first standing acoustic wave.

2. The device according to claim 1, wherein the first wave component is a first wave generator and the second wave component is either a second wave generator, a reflective material, a reflective surface, or a reflective layer.

3. The device according to claim 2, wherein one of the first or second wave components is a reflective surface formed as the first or second surface.

4. The device according to claim 1, wherein a portion of the first surface and the second surface is composed of the phantom material.

5. The device according to claim 4, wherein the phantom material mimics acoustical properties of water.

6. The device according to claim 1, comprising a first inlet for delivering the first inflow stream and a second inlet for delivering the second inflow stream positioned on the second surface near the first end, and a first outlet and a second outlet positioned on the second surface near the second end, wherein the inlets and outlets are in fluid communication with the channel.

7. The device according to claim 6, wherein the device is configured to have the composition introduced into the device through the first inlet and a wash material introduced into the device through the second inlet.

8. The device according to claim 7, wherein the wash material is selected from the group consisting of water, saline, dextrose, saline with 5% dextrose, phosphate buffered saline.

9. The device according to claim 8, wherein the device is configured such that the composition and the wash material are mixed together after being introduced to the device and passing the first planar shelf, and then separated from each other in the separation region of the channel by a pressure node associated with the first standing acoustic wave.

10. A device for washing a multicomponent mixture, the device comprising:
    a body having a first surface, and a second opposing surface;
    a first wave generator coupled to the first surface;
    a wave component selected from the group consisting of a second wave generator, a first reflective material, a first reflective surface, and a first reflective layer, wherein the wave component is coupled to or forms the second surface;
    wherein the body defines a channel having a channel floor, channel walls, and a channel ceiling, the channel extending along the longitudinal axis from a first end region of the device to a second end region of the device, the channel comprising a receiving region near the first end region, a collection region near the second end region, and a separation region between the receiving region and collection region, the separation region being positioned between the first wave generator and the wave component, the receiving region divided into a first inflow region and a second inflow region by a first shelf, the collection region divided into a first outflow region and a second outflow region by a second shelf,
    wherein a first protrusion extends along and is adjacent to a first one of the channel walls within the channel and a second protrusion extends along and is adjacent to a second one of the channel walls within the channel, the first protrusion and the second protrusion extending from the channel floor to the channel ceiling, and
    wherein the channel floor, the first protrusion, the second protrusion, and the channel walls comprise a phantom material.

11. The device according to claim 10, wherein the first wave generator and the wave component generate a standing bulk acoustic wave with a pressure node located in the separation region of the channel.

12. The device according to claim 10, further comprising:
    a first inlet in fluid communication with the first inflow region and the mixing region;
    a second inlet in fluid communication with the second inflow region and the mixing region;
    a first outlet in fluid communication with the first outflow region and the collection region; and
    a second outlet in fluid communication with the second outflow region and the collection region.

13. The device according to claim 12, wherein the device is configured to receive the multicomponent mixture comprising red blood cells through the first inlet and a wash material through the second inlet, wherein the multi component mixture and the wash material are mixed at the mixing region of the channel.

14. The device according to claim 13, wherein the first wave generator and the second wave generator or first reflective material generate a standing bulk acoustic wave with a pressure node positioned in the separation region of the channel, and the pressure node separates the red blood cells from the wash solution.

15. The device according to claim 14, wherein the red blood cells exit the device through the first outlet and the wash material exits the device through the second outlet.

16. The device according to claim 10, wherein the phantom material mimics the acoustic properties of water.

17. The device according to claim 10, wherein the separation channel has a length of from about 20 mm to about 100 mm, a width from about 5 mm to about 50 mm, and a height of from about 0.5 mm to about 3 mm.

18. A device for washing a composition comprising red blood cells, the device comprising:
    a plurality of layers defining a channel having a mixing region, a separation region, and a collection region, a first layer of the plurality of layers extending into the mixing region and isolating a first inlet from a second inlet, the first inlet and the second inlet open to the mixing region, the mixing region open to the separation region, the separation region in fluid communication with the collection region;
    a first sidewall located within the channel along a first side of the channel and extending along a longitudinal axis of the channel;
    a first protrusion extending from a bottom layer of the plurality of layers to a top layer of the plurality of layers and along and adjacent to the first sidewall;
    a second sidewall located within the channel along a second side of the channel and extending along the longitudinal axis, the first sidewall and the second sidewall being a phantom material;
    a second protrusion extending from the bottom layer of the plurality of layers to the top layer of the plurality of layers and along and adjacent to the second sidewall;
    a first wave component coupled to a first surface of the channel; and
    a second wave component coupled to a second surface of the channel, the second surface parallel to the first surface,
    wherein the separation region of the channel is positioned between the first wave component and the second wave component, and wherein the first wave component and second wave component are configured to generate a first standing acoustic wave.

19. The device according to claim 18, wherein the first wave component is a first wave generator and the second wave component is either a second wave generator, a reflective material, a reflective surface, or a reflective layer.

20. The device according to claim 18, wherein one of the first or second wave components is a reflective surface formed as the first or second surface.

21. The device according to claim 18, wherein a portion of at least one of the first surface or the second surface is composed of the phantom material.

22. The device according to claim 21, wherein the phantom material mimics acoustical properties of water.

* * * * *